(12) United States Patent
Gill et al.

(10) Patent No.: US 8,226,651 B2
(45) Date of Patent: Jul. 24, 2012

(54) PATIENT FRAME CONSTRUCTED FROM COMPOSITE MATERIAL

(75) Inventors: Steven Streatfield Gill, Bristol (GB); Andrew Paul Godbehere, Winscombe (GB)

(73) Assignee: Elekta AB, Stockholm (SE)

( * ) Notice: Subject to any disclaimer, the term of this patent is extended or adjusted under 35 U.S.C. 154(b) by 1935 days.

(21) Appl. No.: 10/469,729

(22) PCT Filed: Feb. 27, 2002

(86) PCT No.: PCT/GB02/00856
§ 371 (c)(1),
(2), (4) Date: Feb. 10, 2004

(87) PCT Pub. No.: WO02/069827
PCT Pub. Date: Sep. 12, 2002

(65) Prior Publication Data
US 2004/0116925 A1    Jun. 17, 2004

(30) Foreign Application Priority Data

Mar. 2, 2001    (GB) .................................. 0105317.2

(51) Int. Cl.
*A61B 17/00* (2006.01)
(52) U.S. Cl. ........................................ 606/54; 600/415

(58) Field of Classification Search .................. 600/415, 600/417, 423; 606/54, 130, 56; 602/17, 602/18
See application file for complete search history.

(56) References Cited

U.S. PATENT DOCUMENTS

| | | | | |
|---|---|---|---|---|
| 3,876,607 | A | * | 4/1975 | Snell et al. .................... 523/445 |
| 4,269,759 | A | * | 5/1981 | Edelman ....................... 523/468 |
| 4,612,930 | A | * | 9/1986 | Bremer ......................... 606/130 |
| 4,706,665 | A | * | 11/1987 | Gouda .......................... 606/130 |
| 4,740,343 | A | * | 4/1988 | Gaku et al. .................... 264/225 |
| 5,337,760 | A | | 8/1994 | Nichols |
| 5,681,326 | A | | 10/1997 | Lax |
| 6,419,636 | B1 | * | 7/2002 | Young et al. .................. 600/549 |
| 2002/0018941 | A1 | * | 2/2002 | Matsumoto et al. .............. 430/5 |
| 2003/0170306 | A1 | * | 9/2003 | Raether et al. ................ 424/484 |

FOREIGN PATENT DOCUMENTS

GB      2213066      8/1989

OTHER PUBLICATIONS

The Practice of Neurosurgery, Tindall, et al. vol. I (1996).

* cited by examiner

*Primary Examiner* — Victor Nguyen
(74) *Attorney, Agent, or Firm* — Kohn & Associates, PLLC

(57) ABSTRACT

The present invention relates to a frame for attaching to a patient. The present invention also relates to a stereoguide and a member for attaching to a patient. The present invention also relates to a method for manufacturing the frame, member and stereoguide of the present invention. The frame, member and stereoguide are constructed from a composite material comprising a matrix material and electromagnetically inert fibers.

21 Claims, 3 Drawing Sheets

During cure

Machine tool

PATIENT FRAME CONSTRUCTED FROM COMPOSITE MATERIAL

CROSS-REFERENCE TO RELATED APPLICATIONS

This patent application is a National Phase filing of PCT/GB02/00856, filed Feb. 27, 2002, which claims the benefit of priority of Great Britain Patent Application Serial No. 0105317.2, filed Mar. 2, 2001, all of which are incorporated herein by reference.

TECHNICAL FIELD

The present invention relates to a frame for attaching to a patient. The present invention also relates to a stereoguide and a member for attaching to a patient. The present invention also relates to a method for manufacturing the frame, member and stereoguide of the present invention.

DESCRIPTION OF RELATED ART

Frames and members are used in a variety of techniques in order to immobilize certain parts of the body or to act as a platform from which to direct instruments to a desired target.

In particular, a neurosurgical stereotactic frame in combination with a stereoguide is used for locating and guiding instruments to specific targets in the brain of a patient identified using diagnostic imaging techniques.

Over the past decade there has been an exponential expansion of image directed neurosurgery. Frameless stereotaxy in particular, has now become routine in most neurosurgical centers for resecting tumors but its limited operational accuracy makes it unsuitable for functional neurosurgery and radiosurgery, and for biopsing brain-stem targets. For these latter procedures, that require considerable precision, the use of a stereotactic frame is essential as it ensures fixation of the head during imaging acquisition and treatment and provides a stable platform from which to direct instruments to the target with millimeter accuracy using a stereoguide.

Generally, stereotactic frames are made from aluminum. A frame made of carbon fiber composites is also known. While such frames are generally acceptable for ventriculography or x-ray Computerized Tomography (CT) based stereotaxy, because they are conductive, they cause artifacts on magnetic resonance (MR) images due to absorption and distortion of signal with consequent loss of sensitivity, spatial resolution and accuracy. For similar reasons, frames containing electromagnetic conducting materials produce poor images using high field magnetic resonance imaging such as for functional MRI (FMRI) and Magnetic Resonance Spectroscopy (MRS) as well as when using magneto encephalography (MEG).

A frame constructed of aluminum or other metal will absorb X-rays and γ rays and will therefore have a deleterious effect on images acquired using Positron Emission Tomography (PET), Single Photon Emission Computerized Tomography (SPECT), and to some degree X-ray imaging including Computerized Tomography (CT).

In numerous surgical procedures, it is essential that the frame, member or stereoguide is rigid. For example, where the frame or member acts as a platform from which instruments are directed to a target, it is essential that the frame or member is sufficiently rigid so as not to bend or flex during the procedure and thereby enabling the accurate placement of the instruments. This is particularly important where the frame is a stereotactic frame used in neurosurgery for accurately targeting instruments to a target site generally only a few millimeters in diameter.

In some procedures it is also desirable to sterilize the frame, member or stereoguide.

Generally sterilization is achieved via autoclaving.

The present invention overcomes at least some of the problems associated with the prior art frames, members and stereoguides.

SUMMARY THF INVENTION

The present invention provides a rigid electromagnetically inert frame for attaching to a patient, wherein the frame is constructed from a composite material comprising a matrix material and electromagnetically inert fibers.

By ensuring that the frame is non-metallic and electromagnetically inert it will not significantly absorb or distort the electromagnetic waves (e.g. X-rays, y rays or radiowaves) whose detection facilitates the formation of images in biomedical imagers.

The images will therefore be sharper and less distorted than those obtained with frames made of conventional materials.

Neurosurgeons and radiosurgeons can exploit the sharp high resolution images for more accurate and safer surgical procedures, in particular stereotactic procedures. If the frame is a stereotactic frame used to obtain images under stereotactic conditions, the ability to obtain sharp high resolution and undistorted images is invaluable in planning surgery in eloquent areas and in localizing epileptic foci and functional abnormalities for targeted treatment. The frame must be sufficiently rigid so that any measurement taken using the frame will consistently identify the same target site with less than +/−1 mm variability.

Preferably, the frame has a rigidity equivalent to aluminum. It is further preferred that the frame at room temperature has a Young's module of at least 20 GPa.

The term "frame" refers to any structure which can be attached to a patient and which acts as a platform from which instruments can be directed to a target of interest or which can be used to support or immobilize a part of a patient's body. The term "immobilize a part of a patient's body" means preventing or restricting movement of that part of the patient's body in at least one direction.

As the frame is electromagnetically inert and therefore non-metallic, it will not impair the quality or cause distortion of biomedical images obtained using CT, MRI, FMRI, MRS, MEG, PET or SPECT scanning. The term "non-metallic" means that the frame does not comprise metal.

In terms of electromagnetic characteristics, the frame preferably has a Dielectric constant of less than 4 Dk and/or a Loss Tangent of less than 0.04 Df.

The matrix material can be any material suitable for forming the rigid electromagnetically inert frame of the present invention. Preferably the matrix material is an epoxy resin with a cure temperature of about 120° C. or more. It is further preferred that the matrix material is any material which has a wet glass transition temperature of greater than 137° C. It is further preferred that the matrix material is an epoxy resin with a cure temperature of about 180° C. or more. It is most preferred that the matrix material is a cyanate ester material. Preferably the cyanate ester material has a cure temperature of about 177° C. (+/−10 C).

In a number of situations it will be desirable to sterilize the frame of the present invention. Sterilization can be achieved using chemicals but is preferably achieved by autoclaving the frame. Accordingly, and as indicated above, preferably the matrix material has a wet glass transition temperature (the temperature at which the resin becomes soft) of greater than 137° C. By using such a matrix material the frame will maintain its shape on autoclaving.

Preferably the composite material used to construct the frame of the present invention has a moisture absorption value of less than 3% at saturation. A low moisture absorption value is also desired when the frame is to be autoclaved.

The electromagnetically inert fibers can be any electromagnetically inert fibers suitable for producing the rigid frame of the present invention. Preferably the fibers have dielectric constant of less than 40 Dk and/or a loss tangent of less than 0.04 Df. Preferably, the electromagnetically inert fibers are glass fibers or Quartz fibers.

It is further preferred that the composite material used to construct the frame of the present invention comprises the matrix material and the electromagnetically inert fibers at a ratio of 40%±10% by volume.

In a preferred embodiment, the frame of the present invention is a stereotactic frame. The frame of the present invention is constructed from a material that causes no artifact on biomedical images, can be manufactured to acceptable dimensional tolerances, is resistant to distortion from normal use, can be sterilized by autoclaving and/or chemical treatment and remains dimensionally stable. It is also preferred that the stereotactic frame be connected to a stereoguide which is constructed from a composite material comprising the matrix material and electromagnetically inert fibers described above in connection with the frame of the present invention.

The term "stereotactic frame" refers to any frame which can be used to locate a target site within a 3D space. Preferably the stereotactic frame comprises a base ring and fixing elements for attaching the stereotactic frame to a patient. The fixing elements are preferably posts extending substantially perpendicularly away from the plane of the base ring. Both the base ring and the fixing elements are constructed from the composite material. Stereotactic frames are well known to those skilled in the art and are described in Stereotactic and Functional Neurosurgery/The Practice of Neurosurgery Part XI/Editors G. T. Tindall, P. R. Cooper, D. L. Barrow: Williams & Wilkins 1996.

In use the stereotactic frame holds the desired part of the patient, usually the head, in a CT, MRI, FMRI, MRS, MEG, PET, SPECT or similar scanner. The image produced using the stereotactic frame of the present invention is not substantially geometrically distorted, degraded or altered by the presence of the frame.

In an alternative embodiment, the frame is a halo for use with apparatus for immobilizing the head of the patient, generally, with respect to the shoulders of the patient. Haloes are well known to those skilled in the art and are described in Spinal Orthoses, Chapter 172. The Practice of Neurosurgery/ Editors G. T. Tindall, P. R. Cooper, D. L. Barrow: Williams & Wilkins 1996.

The present invention also provides a rigid electromagnetically inert stereoguide constructed from the composite material used to construct the frame of the present invention. Stereoguides are well known to those skilled in the art and are described in Stereotactic and Functional Neurosurgery/The Practice of Neurosurgery Part XI/Editors G. T. Tindall, P. R. Cooper, D. L. Barrow: Williams & Wilkins 1996.

The stereoguide, shown generally at 8 in FIG. 4, typically comprises an arc that is fixed to the frame with bars that engage with lockable slides. The slides facilitate displacement of the arc in 3 spatial planes (anteroposterior, lateral and vertical) relative to the frame. The slides are scaled in millimeters and enable the center of the arc to be positioned at the calculated target co-ordinates. The arc can be pivoted 180 degrees and a moveable carriage fixed to its perimeter will guide a probe to its center thus allowing the surgeon to choose multiple trajectories to the target.

With the exception of the locking mechanism for the slides and the moveable carriage for the probe, the stereoguide may be constructed entirely from the composite material of the present invention with the scales laser etched into the material. The locking mechanism for the slides and the moveable carriage for the probe are generally constructed from aluminum. Although aluminum is not electromagnetically inert, by considerably reducing the amount of aluminum present significant improvements in the quality of the images are obtained.

The present invention also provides a rigid electromagnetically inert member for attaching the frame of the present invention to a patient, wherein the member is constructed from the composite material used to construct the frame of the present invention. The member does not substantially distort images produced by a magnetic resonance scanner, and preferably has a maximum distortion of 2 mm or 4° once applied to the patient.

The rigid member can be any member for attaching to a patient. In particular, the rigid member can be a threaded pin having a main body which engages with the frame and a tip which engages the head of a patient. The main body of the threaded pin is constructed from the composite material and the tip is constructed from metal (e.g. titanium) or ceramic.

The rigid member can also be a rod having a main body for engaging the frame and a reduced diameter end for insertion into a drill hole formed in the skull of a patient. The entire rod is made from the composite material.

Preferably the member of the present invention is capable of being attached to a desired part of the patient and is substantially immobilized relative to the desired part of the patient. The term "substantially immobilized" means that the member can be moved by less than 2 millimeters relative to the part of the patient to which the member is attached.

The present invention also provides a method for manufacturing the frame, stereoguide or member of the present invention comprising laminating laminate elements comprising the matrix material and electrically inert fibers, into or around a mold and curing the matrix material.

The mold may be a male tool mold around which are laminated the laminate elements or a female tool mold in which the laminate elements are laminated. The male tool mold defines the inner surface of the frame, member or stereoguide. The female tool mold defines at least the outer surface of the frame, member or stereoguide. Preferably the mold is a male tool mold and the laminate elements are laminated around the male tool mold in the shape of a closed loop. A vacuum bag may also be used wherein the bag is sealed to the tool mold to isolate the laminate from the atmosphere during processing.

In order to provide additional strength at certain parts of the frame, stereoguide or member of the present invention, additional laminate elements can be positioned at sites where additional strength is required.

The matrix material can be cured using any method such as autoclaving, resin transfer or vacuum molding techniques.

On curing the composite material, an exothermic reaction occurs resulting in the production of excess heat. This excess heat, if not controlled, can lead to damage to the composite material as well as damage to the mold. In order to avoid damage occurring by the production of heat exothermically, it is preferred that the method comprises introducing temperature plateaus early in the curing cycle. It is further preferred that sensors are positioned in or adjacent to the laminated material to sense overheating of the laminated material during the curing cycle. The sensors can feed back to the heating equipment and thereby control the curing temperature.

It is further preferred that the mold has a high thermal conductivity and/or a high thermal mass. By ensuring that the mold has a high thermal conductivity and/or a high thermal mass, any excess heat produced during the curing cycle can be "absorbed" via the mold acting as a heat sink without leading to deleterious effects on the composite material.

Where there are recesses or protrusions on the frame, stereoguide or member of the present invention, it is preferred that these features are produced by carefully laminating small laminate elements to form the recess or protrusion. By using short laminates initially, it is ensured that the material flows into the recess or protrusion more effectively. Furthermore, debulking operations can be performed while the material is being laminated in order to ensure that good definition of the recess or protrusion can be achieved.

The method of producing the frame, guide or member may comprise laminating the laminate elements and then performing one curing cycle in order to produce the composite material. Alternatively, the frame, stereoguide or member can be built up in stages comprising laminating and curing a number of layers until the frame, stereoguide or member is complete. The advantage of building up the frame, stereoguide or member in stages is that the amount of heat produced during the curing cycle is reduced.

The method of the present invention preferably further comprises machining the cured composite material to the desired dimensions. Machining processes are well known to those skilled in the art.

In a preferred embodiment, the frame of the present invention may be formed by forming a long tube like structure of the composite material and subsequently machining this tube like structure into a number of individual frames (see FIG. 1). This has the advantage of simplifying the laminating process by reducing the number of small, difficult to position, individual laminates.

Preferably the machining methods produce a frame, stereoguide or element having the required accuracy as determined by the use of the frame, stereoguide or member. Preferably, the machining methods are accurate to within +/−0.1 mm.

The present invention also provides a method for producing a diagnostic image of a patient having the frame, stereoguide or member of the present invention attached, comprising taking a diagnostic image of the patient and the frame, stereoguide or member Preferably the diagnostic image is produced by CT, MRI, FMRI, MRS, MEG, SPECT or PET scanning. The image may also be produced by an x-ray.

BRIEF DESCRIPTION OF THE DRAWINGS

Embodiments of the present invention will now be described by way of example only and with reference to the accompanying drawings, in which.

BRIEF DESCRIPTION OF THE INVENTION

Example

Manufacture of a Stereotactic Frame

Figure 1:
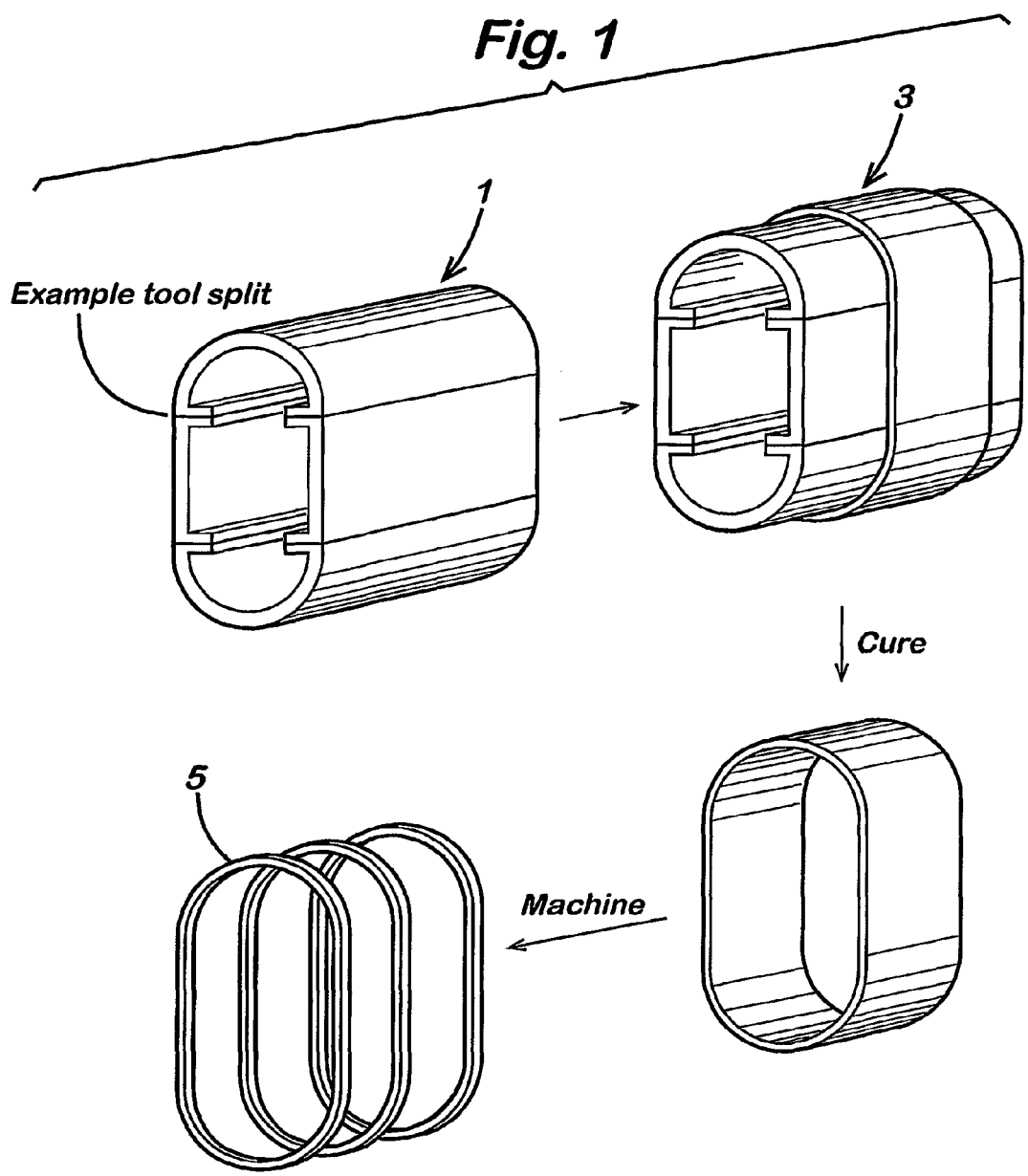
FIG. 1 shows schematically the process for producing a stereotactic frame. Please note, mounting details and other features of the frame are not shown in the figure.

A composite material is supplied as a prepreg (resin impregnated fibers in an uncured state), also referred to herein as a laminate element (7). The prepreg (7) is laminated onto a mold (1) surface, placed in a vacuum environment, pressure applied to the laminate (3) and heated through a cycle to result in curing of the resin. The component produced is then removed from the mold and machined to final shape. See FIG. 1.

All laminating activities are completed in a 'clean room' environment in which the room temperature and humidity are controlled, and all surfaces are clean from dust and other potential contaminants. A male mold tool (1) is used to define the inner profile of the frame (5). Alternatively a female tool may also be used. No more that 4 layers or 0.5 mm stacked thickness of prepreg (7) layers are laminated on to the mold tool (1) to the required configuration (fiber orientation). A sealing bag is then attached to or wholly encompasses the mold tool (1) and all atmosphere is drawn from the 'vacuum bag' in order to evacuate the laminated assembly. The assembly is left in this evacuated state for 30 minutes. This is known as a 'debulking' procedure and is repeated every 4 additional layers or every additional 0.5 mm, whichever is soonest. It acts to consolidate the assembly.

Figure 2:
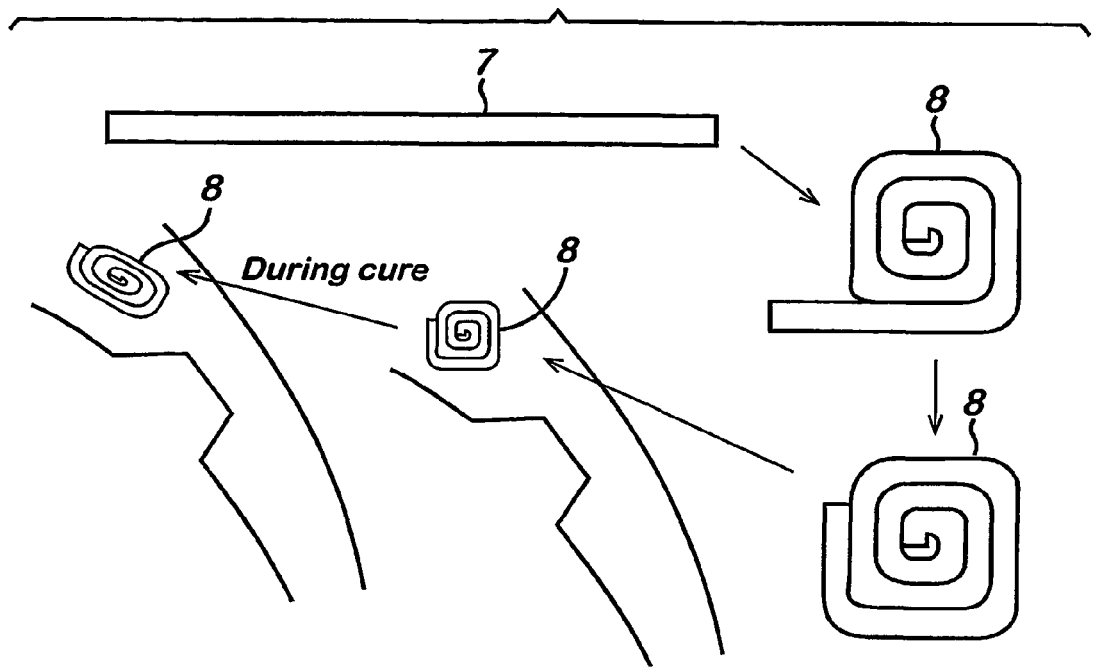
FIG. 2 shows the positioning of additional laminate elements at positions within the stereotactic frame which require additional strength.

Through repetition of this procedure the component thickness and fiber orientation is built up. In particularly thick areas inserts may be used. These are in the form of separately consolidated prepreg (8) assemblies, either layered or rolled in construction. See FIG. 2.

In order to change the thickness of the component in a certain areas the prepreg layers (7) are staggered to increase the thickness gradually from one area to another. Such stacks are then covered by no less that one final layer to embody them within the bulk of the laminate (3), i.e. none being visible on any surface.

Once the laminating process is ended and the laminate (3) finally consolidated then the assembly is prepared for curing. A consolidation tool, be it rubber, elastomer, metallic or composite is placed on the component surface. Breather and bleeder materials are used in the vacuum bag assembly and the final, curing vacuum bag is applied and sealed. Thermocouples are strategically placed, particularly near areas of largest thickness, within the assembly. The assembly is then placed in an autoclave and cured.

The curing cycle consists of initially attaining full vacuum in the vacuum bag (full vacuum equating to no less than 0.85 atmospheres). Once achieved the autoclave is then pressurized, typically to 100 psi, but no less that 60 psi. On reaching no less than 40 psi the vacuum bag is vented to atmosphere. The autoclave is heated at a target of 2° C./minute up to 120° C., starting with the autoclave pressurization process. The temperature is then maintained at 120° C. for no less than 30 minutes. This is in order to avoid 'exotherm', self heating of the component by the exothermic energy produced by the cross-linking action of the matrix material. Should excessive heat-up become evident then the thermocouples sense early exothermic activities and the autoclave temperature cycle is modified by the autoclave control systems to reduce as appropriate, the energy input into the assembly. Once the cure cycle 'dwell' is complete the assembly is heated to the final curing temperature, typically 180° C., where it is held until the component is cured, typically for 1-2 hours. The component is then cured to room temperature over a period of no less than 1 hour but typically taking several hours.

Figure 3:
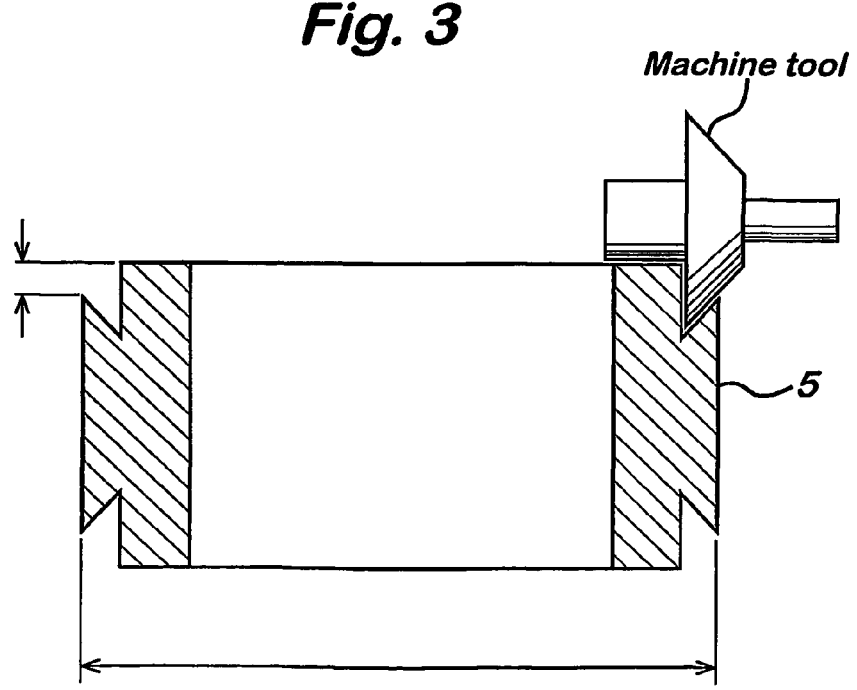
FIG. 3 shows schematically a method for machining the stereotactic frame.
Figure 4:
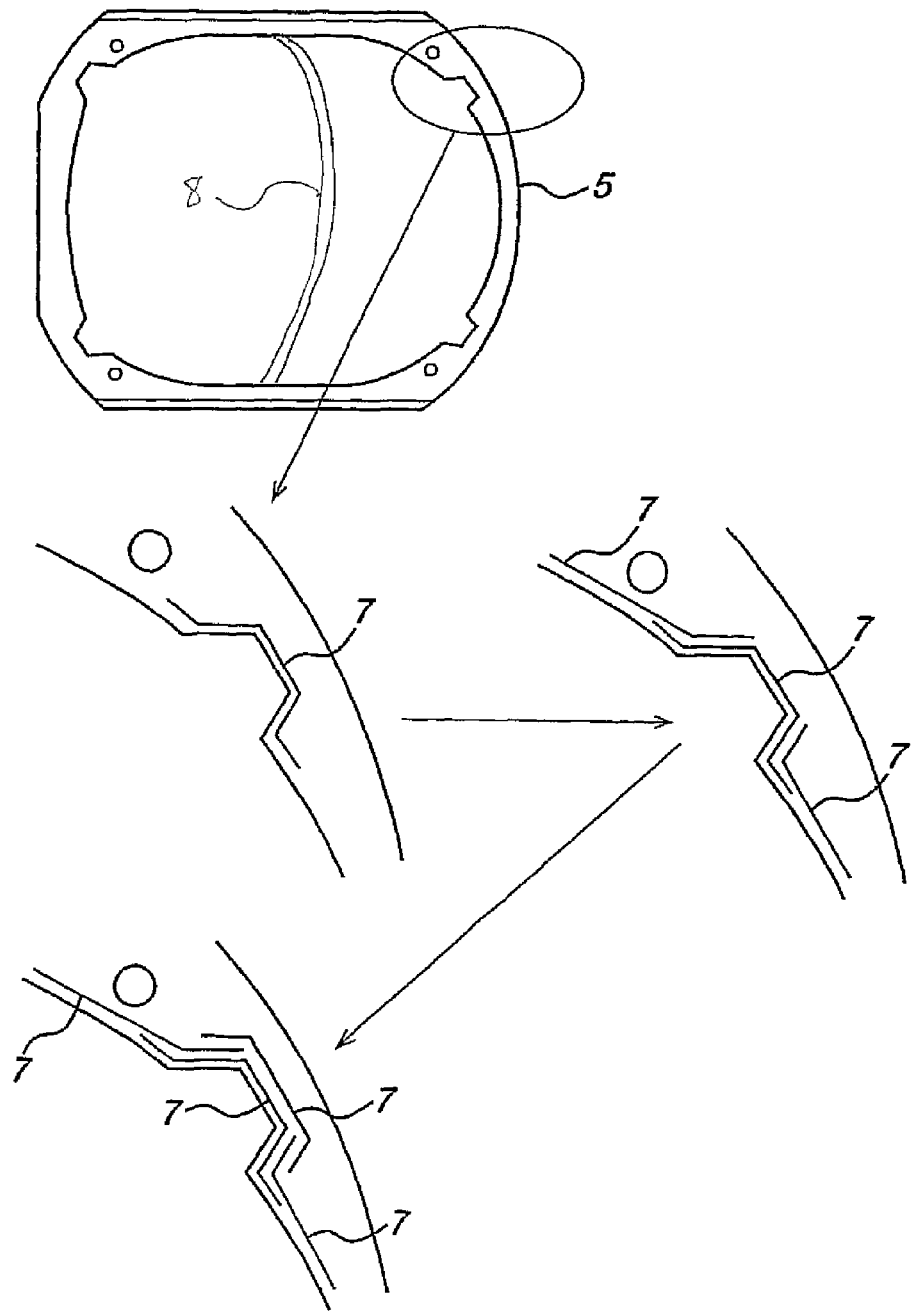
FIG. 4 shows schematically the positioning of short laminate elements in order to ensure material consolidation in a corner of the mold.

Once at room temperature the component is removed from the tool (1) and all vacuum bag materials removed. The cured component is then machined to the final component shape. See FIG. 3. This requires vented equipment and specialist cutters due to the potentially toxic nature of the operation and the high machining accuracies required, generally to tolerances of greater than ±0.1 mm.

Where several frames (5) are laminated in one operation, and thereby forming a single tube-like molding, each frame (5) must firstly be machined from the single tube-like molding.

The component is painted and graticules marked using standard techniques. The mold tool (1) is cleaned and releasing wax or other treatment applied such that the component can be readily removed from the mold (1) post curing.

It will be apparent to those skilled in the art that the actual cure cycle depends upon the materials used and their exothermic and curing characteristics. The cycles above are illustrative.

The mold tool (1) must be split in order to facilitate removal of the component post cure, or else it must have expanding components which shrink upon cooling (such as elastomeric tooling) to aid release of the cured laminate (3) such as elastomeric tooling.

A female tool can be used, but consolidation difficulties may occur. This can be overcome with use of an expanding male insert.

The laminates (7) are laid so that no single laminate (7) forms greater than half of the component circumference. This is to put joints in to the laminate assembly (3) which aids consolidation during the cure cycle. Such joints (i.e. an overlap of one laminate (7) with the next) must be no less than 10 mm and are generally placed in areas of maximum component thickness.

The laminate (7) may be unidirectional or woven, i.e. the fibers may all align, or be of a woven form. Once laid successively to a predetermined orientation the frame strength and stiffness is determined in accordance with standard techniques.

What is claimed is:

1. A rigid frame for attaching to a patient, wherein the frame is electromagnetically inert and is constructed from a composite material comprising a matrix material and electromagnetically inert fibers, wherein the matrix material has a wet glass transition temperature of greater than 137 degree Celsius; wherein the electromagnetically inert fibers have dielectric constant of less than 40 Dk and/or a loss tangent of less than 0.04 Df; and wherein the ratio of matrix material to electromagnetically inert fibers is 40% by volume.

2. The frame of claim 1, wherein the frame is capable of being attached to a desired part of the patient and is substantially immobilized relative to the desired part of the patient.

3. The frame of claim 1, wherein the frame is a stereotactic frame.

4. The frame of claim 3, wherein the stereotactic frame is connected to a stereoguide constructed from a composite material comprising a matrix material and electromagnetically inert fibers, wherein the matrix material has a wet glass transition temperature of greater than 137° C.

5. The frame of claim 1, wherein the frame is a halo.

6. A rigid stereoguide constructed from a composite material comprising a matrix material and electromagnetically inert fibers, wherein the matrix material has a wet glass transition temperature of greater than 137° C. and the rigid stereoguide is electromagnetically inert; wherein the composite material has a moisture absorption value of less than 3% at saturation; wherein the electromagnetically inert fibers have dielectric constant of less than 40 Dk and/or a loss tangent of less than 0.04 Df.

7. Any one of the frame of claim 1, the stereoguide of claim 6, wherein the matrix material is an epoxy resin with a cure temperature of about 120° C. or more.

8. Any one of the frame of claim 1, the stereoguide of claim 6, wherein the matrix material is an epoxy resin with a cure temperature of about 180° C. or more.

9. Any one of the frame of claim 1, the stereoguide of claim 6, wherein the matrix material is a cyanate ester matrix material with a cure temperature of about 177° C.

10. Any one of the frame of claim 1, or the stereoguide of claim 6, having a rigidity equivalent to aluminum.

11. Any one of the frame of claim 1, the stereoguide of claim 6, having a Young's module of at least 20 Gpa.

12. Any one of the frame of claim 1, the stereoguide of claim 6, wherein the electromagnetically inert fibers are glass fibers.

13. A method for manufacturing any one of the frame of claim 1, the stereoguide of claim 6, comprising laminating laminate elements comprising the matrix material and electrically inert fibers into or around a mold and curing the matrix material.

14. The method according to claim 13, wherein the laminate elements are laminated in the shape of a closed loop on a male tool mold and cured.

15. The method of claim 13, wherein one or more additional laminate elements are positioned at sites in the frame, stereoguide or member where additional strength is required.

16. The method of claim 13, wherein the matrix material is cured by introducing temperature plateaus early in the curing cycle.

17. The method of claim 13, wherein sensors are positioned in or adjacent the laminated material to sense overheating of the laminated material during the curing cycle.

18. The method of claim 17, wherein the sensors feedback to control the curing temperature.

19. The method of claim 13, wherein the mold has high thermal conductivity and/or high thermal mass.

20. The method of claim 13, wherein the frame, stereoguide or member are built up in stages comprising laminating and curing a first part of the frame, stereoguide or member, and then laminating and curing one or more subsequent parts of the frame, stereoguide or member.

21. The method of claim 13 additionally comprising the step of machining the cured composite material to the desired dimensions.

* * * * *